(12) United States Patent
Farina

(10) Patent No.: US 7,672,478 B2
(45) Date of Patent: *Mar. 2, 2010

(54) SPRAY DATA ACQUISITION SYSTEM

(75) Inventor: Dino J. Farina, Holliston, MA (US)

(73) Assignee: Proveris Scientific Corporation, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/291,492

(22) Filed: Nov. 10, 2008

(65) Prior Publication Data

US 2009/0136086 A1    May 28, 2009

Related U.S. Application Data

(63) Continuation of application No. 10/895,745, filed on Jul. 20, 2004, now Pat. No. 7,463,751, which is a continuation of application No. 09/640,246, filed on Aug. 16, 2000, now Pat. No. 6,785,400.

(60) Provisional application No. 60/149,281, filed on Aug. 17, 1999.

(51) Int. Cl.
*G06K 9/00* (2006.01)
*G01N 21/00* (2006.01)
*B05B 5/00* (2006.01)

(52) U.S. Cl. .................. 382/100; 356/436; 239/692

(58) Field of Classification Search .................. 382/100; 356/27, 336, 339, 414, 436, 437, 438; 424/1.13, 424/59, 76.2, 84, 404, 426, 489; 239/130, 239/380, 692, 695, 701, 706; 73/1.02, 1.37, 73/1.41; 700/282, 283
See application file for complete search history.

(56) References Cited

U.S. PATENT DOCUMENTS

| 3,275,744 A | 9/1966 | Dietrich |
| 4,004,550 A | 1/1977 | White et al. |
| 4,357,670 A | 11/1982 | McFarlane |
| 4,415,265 A | 11/1983 | Campillo et al. |

(Continued)

FOREIGN PATENT DOCUMENTS

| JP | 52 063750 A | 5/1977 |
| WO | WO 92/07600 A | 5/1992 |
| WO | WO 02/100468 A | 12/2002 |
| WO | WO 03/000429 A2 | 1/2003 |

OTHER PUBLICATIONS

Date of Mailing, Feb. 17, 2009, Minutes of the Oral Proceedings before the Examining Division, Application No. 00 967 400.3
Date of Mailing, Feb. 25, 2009, Communication under Rule 71(3) EPC, Application No. 00 967 400.3.

(Continued)

*Primary Examiner*—Abolfazl Tabatabai
(74) *Attorney, Agent, or Firm*—Hamilton, Brook, Smith & Reynolds, P.C.

(57) ABSTRACT

A spray data acquisition system includes a spray pump actuator that is capable of providing a pumping force to a pumping device to generate an aerosol spray plume along a spray axis. The system also includes an illumination device that illuminates the aerosol spray plume along at least one first geometric plane that intersects the aerosol spray plume. The system further includes an imaging device that acquires data representative of an interaction between the illumination and the aerosol spray plume along at least one geometric plane.

10 Claims, 3 Drawing Sheets

U.S. PATENT DOCUMENTS

| | | | |
|---|---|---|---|
| 4,614,300 | A | 9/1986 | Falcoff |
| 4,628,465 | A | 12/1986 | Ito et al. |
| 4,965,841 | A | 10/1990 | Kaneko et al. |
| 4,984,158 | A | 1/1991 | Hillsman |
| 4,992,952 | A | 2/1991 | Sasaki |
| 5,075,014 | A | 12/1991 | Sullivan |
| 5,284,133 | A | 2/1994 | Burns et al. |
| 5,337,926 | A | 8/1994 | Drobish et al. |
| 5,356,049 | A * | 10/1994 | Harris et al. ............. 222/383.1 |
| RE34,910 | E | 4/1995 | Funkenbusch et al. |
| 5,561,527 | A * | 10/1996 | Krone-Schmidt et al. ... 356/414 |
| 5,579,659 | A | 12/1996 | Roberts |
| 5,785,048 | A | 7/1998 | Koerner |
| 5,879,713 | A | 3/1999 | Roth et al. |
| 6,029,600 | A | 2/2000 | Davis |
| 6,148,815 | A | 11/2000 | Wolf |
| 6,149,071 | A * | 11/2000 | MacCallumMhor et al. .. 239/67 |
| 6,193,936 | B1 | 2/2001 | Gardner et al. |
| 6,256,597 | B1 | 7/2001 | Wang et al. |
| 6,508,112 | B1 * | 1/2003 | Verhoeven ............... 73/114.46 |
| 6,651,651 | B1 * | 11/2003 | Bonney et al. ......... 128/200.23 |
| 6,665,421 | B1 | 12/2003 | Farina |
| 6,785,400 | B1 | 8/2004 | Farina |
| 6,799,090 | B2 | 9/2004 | Farina et al. |
| 6,973,199 | B2 | 12/2005 | Farina |
| 7,100,839 | B2 | 9/2006 | Farina et al. |
| 7,463,751 | B2 * | 12/2008 | Farina ........................ 382/100 |
| 2004/0199296 | A1 | 10/2004 | Farina et al. |
| 2004/0258278 | A1 | 12/2004 | Farina |
| 2005/0001054 | A1 | 1/2005 | Farina et al. |
| 2005/0016527 | A1 | 1/2005 | Barger et al. |
| 2005/0077369 | A1 | 4/2005 | Farina et al. |
| 2006/0102808 | A1 | 5/2006 | Farina et al. |
| 2008/0173067 | A1 | 7/2008 | Farina et al. |

OTHER PUBLICATIONS

Strain gauge. (1992). In Academic Press Dictionary of Science and Technology. Oxford: Elsevier Science & Technology. Retrieved Nov. 17, 2008, from http://www.credoreference.com/entry/3163700/.

Bennett, J. S., "An investigation of particle size measurement using non-intrusive optical techniques in a gas turbine combustor," *M.S. Thesis Naval Postgraduate School*, Monterey, CA, 1 pg. (abstract) (Sep. 1985).

Cohen, J. M. and Rosfjord, T. J., "Spray patternation at high pressure," *American Institute of Aeronautics and Astronautics, Inc.*, p. 1 (1989).

Feikema, D. A., "Optical measurements in rocket engine liquid sprays," *In Alabama Univ., Research Reports: 1994 NASA/ASEE Summer Faculty Fellowship Program 6 p (See N95-1896705-80)*, 1 pg. (abstract) (Oct. 1994).

Sassi, G., et al., "Vision system for combustion and diagnosis in gas turbines," *Proc. Spie vol. 2506*, Air Pollution and Visibility Measurements, Fabian, P., et al., Eds., 1 pg. (abstract) (Sep. 1995).

Institute for Liquid Atomization and Spray Systems—North and South America Newsletter #19—Apr. 1995, Edwards, C. F., Ed., pp. 1-5.

Cummings, R. H., et al., "Comparison of Spray Pattern, Plume Geometry and Droplet Sizing by Light-Scattering for Characterization of Nasal Inhalers," *Respiratory Drug Delivery V*, 1996—Magellan Laboratories, Inc., pp. 320-322.

Voges, H., et al., "Spray Imaging Systems for Quantitative Spray Analysis," *The Fifth Conference of ILASS-ASLA*, 3 pp.

The Fifth Conference of ILASS-ASIA Figs. 1-11, 4 pp.

Deljouravesh, R., "An Optical Patternator for Quantitative and On-Line Spray Diagnostics," thesis submitted to the Department of Mechanical Engineering, Queen's University, Kingston, Ontario, Canada, 86 pp. (Oct. 1997).

Chung, I. P., et al., "Characterization of a Spray from an Ultrasonically Modulated Nozzle," *Atomization and Sprays Journal of the International Institutes for Liquid Atomization and Spray Systems*, vol. 7, 2 pp. (1997).

Wang, G., et al., "An Optical Spray Pattern Analyzer," submitted for presentation at *ILASS Americas '97*, Ottawa, Canada, May 18-21, 1997, 8 pp.

Sellens, R., "Optical Patternation in Sprays," 2 pp.

Sellens, R. and Deljouravesh, R., "Non-Orthogonal Optical Spray Pattern Analysis," 4 pp.

"Laser imaging brings sprays into focus," *Laser Focus World*, 4 pp. (1998), http://lfw.pennnet.com/Articles/Article_Display.cfm?Section=Arch... Feb. 3, 2006 7:58 AM.

Eck, C. R., et al., "Plume Geometry and Particle Size Measurements as a Product Development Tool," *Respiratory Drug Delivery VI*:291-295 (1998).

"Updates on Optical Diagnosis of Fuel Spray Patterns," 2 pp. (1999). http://www.nasatech.com/Briefs/DEC99/LEW16882.html.

Locke, R. J., et al. "Non-Intrusive Laser-Induced Imaging for Speciation and Patternation in High Pressure Gas Turbine Combustors," prepared for the Optical Diagnostics for Fluids, Heat, Combustions, and Phtoomechanics of Solids sponsored by the International Society for Optical Engineering, Denver, Colorado, 9 pp. (Jul. 18-23, 1999).

Hicks, Y. R., "Updates on Optical Diagnosis of Fuel Spray Patterns," NASA Tech Briefs, 2 pp (1999).

Locke, R. J., et al., "Optical Diagnosis of High-Pressure Liquid Fuel Sprays," 2 pp., http://www.nasatech.com/Briefs/Mar99/LEW16701.html.

Locke, R. J., et al., "Nonintrusive Laser-Induced Imaging for Speciation and Patternation in High-Pressure Gas Turbine Combustors," *Proc. SPIE. vol. 3783*, 1 pg. (1999).

Locke, R. J., et al., "Non-Intrusive Laser-Induced Imaging for Speciation and Patternation in High Pressure Gas Turbine Combustors," GLTRS, 2 pp (1999).

"Optical Patternator for Rapid Characterization of Sprays," *Aerometrics, Inc.*, 12 pp.

Stein, S. W., et al., "Using a New Spray Pattern Analyzer to Evaluate Nasal Pump Spray Patterns," *Respiratory Drug Delivery*, VIII:319-322 (2002).

Murphy, S. D., et al., "Advances in Research and Development of Respiratory Drug Delivery Devices Using High Speed Imaging Systems," *Respiratory Drug Delivery*, VIII:533-536 (2002).

Gaynor, A. D., "New Spray Characterization Technique," *Spray Technology & Marketing*:36-37 (1996).

Farina, D. J., "Building a Low-Cost Thermal Imaging System," *Sensors Magazine Online*:2-5 (1998).

Krarup, H. G., et al., "The Malvern Spraytec Applied to Pharmaceutical Spray Analysis," *Respiratory Drug Delivery*, VIII:505-508 (2002).

Murphy, S. D., et al., "Non-Invasive Imaging System Implementing Regulatory Guidelines for the Characterization of the Physical Properties of MDIs," *Respiratory Drug Delivery*, IX:597-599 (2004).

Weinstein, C. L. J., et al., "Development of an Automated Digital Spray Pattern Measurement System," *Respiratory Drug Delivery*, VIII:581-583 (2002).

Aumiller, W., et al., "Time Correlation of Plume Geometry and Laser Light Scattering Droplet Size Data," *Respiratory Drug Delivery*, VIII:497-499 (2002).

Evans, R., "Spray Pattern and Plume Geometry," 1-14.

Constant, M., "A Practical Method for Characterizing Poured Beer Foam Quality," *The American Society of Brewing Chemists, Inc.*, 50(2):37-47, (1991).

Ullom, M. J and Sojka, P. E., "A Simple Optical Patternator for Evaluating Spray Symmetry," *Review of Scientific Instruments*, 72(5), 1 p (2001).

Sellens, R. W. and Wang, G., "Advances in Optical Patternation for Sprays, With Applications," *Eighth International Conference on Liquid Atomization and Spray Systems*, 7 pp. (2000).

Minnich, M. G., et al., "Spatial Aerosol Characteristics of a Direct Injection High Efficiency Nebulizer Via Optical Patternation," *Spectrochimica Acta Part B*, 56:1113-1126 (2001).

Berg, T., et al., "Spray Imaging Systems for Quantitative Spray Analysis," *ILASS-Europe*, 3 pp (2001).

Dhand, R., et al., "High Speed Photographic Analysis of Aerosols Produced by Metered Dose Inhalers," *J. Pharm. Pharmacol.*, 40:429-430, (1988).

Dunbar, C.A., et al., "An Experimental Investigation of the Spray Issued from a pMDI Using Laser Diagnostic Techniques," *Journal of Aerosol Medicine*, 10(4):351-368, (1997).

Settles, G.S., "A Flow Visualization Study of Airless Spray Painting," Proceedings of the 10th Annual conference on Liquid Atomization and Spray Systems, ILASS-Americas '07, May 18-21, 1997, Ottawa, Canada, pp. 145-149.

"Image Therm Engineering Ships the First SprayVIEW Nsx System," http://www.imagetherm.com/News Releases.asp. (2001).

"Guidance for Industry—Bioavailability and Bioequivalence Studies for Nasal Aerosols and Nasal Sprays for Local Action" (Draft Guidance), FDA, pp. 1-36, Jun. 1999.

"Guidance for Industry—Metered Dose Inhaler (MDI) and Dry Powder Inhaler (DPI) Drug Product" (Draft Guidance), FDA, pp. 1-62, Oct. 1998.

"Guidance for Industry—Nasal Spray and Inhalation Solution, Suspension, and Spray Drug Products" (Draft Guidance), FDA, pp. 1-43, May 1999.

Dvorak, P., "How to See Aerosol Spray Patterns and Plumes," *Machine Design*, 72(13): 122 (Jul. 6, 2000).

Badreldin, Amira M., "Real-Time Analysis of Fuel Spray Images," *IEEE*, pp. 622-624 (1987).

Lopera, J. F. G., et al., "Improved Entropic Edge-Detection." Paper supported by grant MAR97-0464-C04-02 of Spanish Government. No date given.

Pastor, J.V., et al., "Analysis Methodology of Diesel Spray and Flame by Means of In-Cylinder Endoscopic Imaging," (The Institution of Electrical Engineers). Savoy Place, London: IEE (2000).

Sellens, Rick and Deljouravesh, Rama, "Non-Orthogonal Optical Spray Pattern Analysis," Ninth International Symposium on Applications of Laser Techniques to Fluid Mechanics, Lisbon, Portugal, Jul. 1998.

Sankar, S.V., et al., "Time-Resolved Measurement of Liquid Mass Distribution in a Fuel Injector Spray Using an Optical Patternator,"Institute for Liquid Atomization and Spray Systems, *ILASS Americas '97*, pp. 266-270, Ottawa, ON, Canada, May 18-21, 1997.

Wang, G., et al., "An Optical Spray Pattern Analyzer," Institute for Liquid Atomization and Spray Systems, *ILASS Americas '97*, pp. 261-265, Ottawa, ON, Canada, May 18-21, 1997.

\* cited by examiner

SPRAY DATA ACQUISITION SYSTEM

RELATED APPLICATIONS

This application is a continuation of U.S. application Ser. No. 10/895,745, filed Jul. 20, 2004 now U.S. Pat. No. 7,463,751, which is a continuation of U.S. application Ser. No. 09/640,246, filed Aug. 16, 2000, now U.S. Pat. No. 6,785,400, which claims the benefit of U.S. Provisional Application No. 60/149,281, filed Aug. 17, 1999. This application is related to U.S. application Ser. No. 09/640,346 filed Aug. 16, 2000, now U.S. Pat. No. 6,665,421. The entire teachings of the above applications are incorporated herein by reference.

BACKGROUND OF THE INVENTION

The present invention relates to systems for and methods of characterizing aerosol spray patterns, and more particularly, to systems and methods that illuminate an aerosol spray plume and utilize optical techniques to characterize the associated spray pattern.

The fluid dynamic characterization of the aerosol spray emitted by metered nasal spray pumps and metered dose inhalers is crucial in determining the overall performance of the inhaler as a drug delivery device ("DDD"). In addition to treating direct respiratory ailments, inhaler-based DDDs are now increasingly being used to deliver drugs such as flu vaccines, insulin and migraine headache relievers because they deliver their dose of medication to tissues that can more efficiently absorb the drug and bring relief to patients more conveniently. Spray characterization is also an integral part of the regulatory submissions necessary for Food and Drug Administration ("FDA") approval of research and development, quality assurance and stability testing procedures for new and existing inhaler-based DDDs.

Thorough characterization of the spray's geometry has been found to be the best indicator of the overall performance of most inhaler-based DDDs. In particular, measurements of the spray's divergence angle (plume geometry) as it exits the device; the spray's cross-sectional ellipticity, uniformity and particle/droplet distribution (spray pattern); and the time evolution of the developing spray have been found to be the most representative performance quantities in the characterization of an inhaler-based DDD.

During research and development, these measurements are typically used to optimally match the spray pump's performance characteristics with the fluid properties of the liquid/solid medicine solution, resulting in a more cost-effective and efficient product design. However, accurate, reliable and easy-to-use protocols and a system for inhaler-based DDD spray characterization do not exist. During quality assurance and stability testing, plume geometry and spray pattern measurements are key identifiers for verifying consistency and conformity with the approved data criteria for the inhaler-based DDD.

The currently adopted inhaler spray testing standard that is in use today at pharmaceutical companies involves firing the spray pump at a solid, thin-layer chromatography ("TLC") plate having a coating that fluoresces in response to incident ultraviolet ("UV") radiation. The TLC plate is positioned at a fixed height above the exit port of the pump. The pattern of the spray deposited on the plate is then analyzed.

In a conventional test configuration, the analysis of an exposed plate begins with illumination of the plate with UV radiation. The incident UV radiation causes the plate's coating to fluoresce and helps to highlight the outline of the spray pattern. Marking instruments and mechanical calipers are then used to draw and measure an outline of the deposited patterns on the plate. Measurements of the spray pattern's ellipticity in terms of major- and minor-diameters are recorded.

One disadvantage to this configuration is that the presence of the TLC plate radically alters the natural fluid dynamics of the spray causing it to switch from a free aerosol jet to an impinging jet.

Another disadvantage to this configuration is that a large of amount of the spray particles bounce off the plate, causing artifacts in the pattern that do not exist in an unconstrained spray. This is especially problematic for dry powder-based DDDs because the particles don't tend to stick to the TLC plate at all causing artificially low spray pattern densities to be measured and reported.

Yet another disadvantage to this configuration is that the measurements of the spray pattern are very sensitive to the operator's judgement and prone to low reliability.

A further disadvantage to this configuration is that the associated measurement technique is restricted to measurements only of the static aspects of the spray pattern; it cannot be used to investigate any time-evolving or plume geometry properties of the spray.

It is an object of the present invention to substantially overcome the above identified disadvantages and drawbacks of the prior art.

SUMMARY OF THE INVENTION

In one preferred embodiment, the invention provides a device for producing image data representative of at least one sequential set of images of a spray plume. Each of the images is representative of a density characteristic of the spray plume (i) along a geometric plane that intersects the spray plume, and (ii) at a predetermined instant in time. The device includes an illuminator for providing an illumination of the spray plume along at least one geometric plane that intersects the spray plume. The device also includes a transducer for generating the image data representative of an interaction between the illumination and the spray plume along the geometric plane.

The foregoing and other objects are achieved by the invention which in one aspect comprises a spray data acquisition system that includes a housing for supporting a pumping device. The pumping device is responsive to an applied force to generate an aerosol spray plume through an exit port thereon along a spray axis. The system further includes a spray pump actuator that is capable of controlling the pumping force and the duration of the aerosol spray plume produced by the pumping device. The system also includes an illumination device that illuminates the aerosol spray plume along at least one first geometric plane that intersects the aerosol spray plume. The system further includes an imaging device that acquires data representative of an interaction between the illumination and the aerosol spray plume along at least one geometric plane.

In another aspect, the invention comprises an apparatus for producing image data representative of at least one sequential set of images of a spray plume. Each of the images is representative of a density characteristic of the spray plume (i) along a geometric plane that intersects the spray plume, and (ii) at a predetermined instant in time. The apparatus includes an illuminator for providing an illumination of the spray plume along at least one geometric plane that intersects the spray plume. The apparatus further includes a transducer for generating the image data representative of an interaction between the illumination and the spray plume along the at least one geometric plane.

In another embodiment of the invention, the sequential set of images is representative of a progression in time.

In another embodiment of the invention, a first time-sequential set of images corresponds to an axial cross-sectional density characteristic along a first geometric plane substantially normal to a flow direction centerline, and a second time-sequential set of images corresponds to a longitudinal density characteristic along a second geometric plane substantially parallel to and intersecting the flow direction centerline.

In another embodiment of the invention, the interaction between the illumination and the spray plume includes optical scattering.

In another embodiment of the invention, the interaction between the illumination and the spray plume includes optical absorption.

In another embodiment of the invention, the transducer includes a digital imaging system for generating and recording the image data.

In another embodiment of the invention, the digital imaging system includes an image sampling rate of approximately 500 images per second.

In another embodiment of the invention, the illuminator includes a laser system having a fan-shaped output pattern.

In another embodiment of the invention, the fan-shaped output pattern includes a fan angle of approximately 45 degrees, and a laser line thickness of approximately one millimeter, measured at the centerline of the spray.

In another embodiment of the invention, the laser system includes a 4 watt, 810 nm laser output.

In another embodiment of the invention, the illumination device illuminates the spray plume along a second geometric plane that intersects the aerosol spray plume, and the imaging device acquires data representative of a second interaction between the illumination and the aerosol spray plume along a second geometric plane. In one embodiment, the first and the second geometric planes are substantially orthogonal.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The spray data acquisition system of the present invention provides images of the time-evolution, particle distribution, and divergence angle of aerosol sprays. The spray data acquisition system is a non-intrusive, optical-based design system that is capable of capturing information representative of the time evolution of an aerosol spray for substantially complete geometrical (divergence angle and plume geometry) and pattern (cross-sectional uniformity and ellipticity) imaging. The modular hardware of the system allows easy customization to meet the needs of a variety of spray testing applications in research & development, stability testing and production environments.

Figure 1:
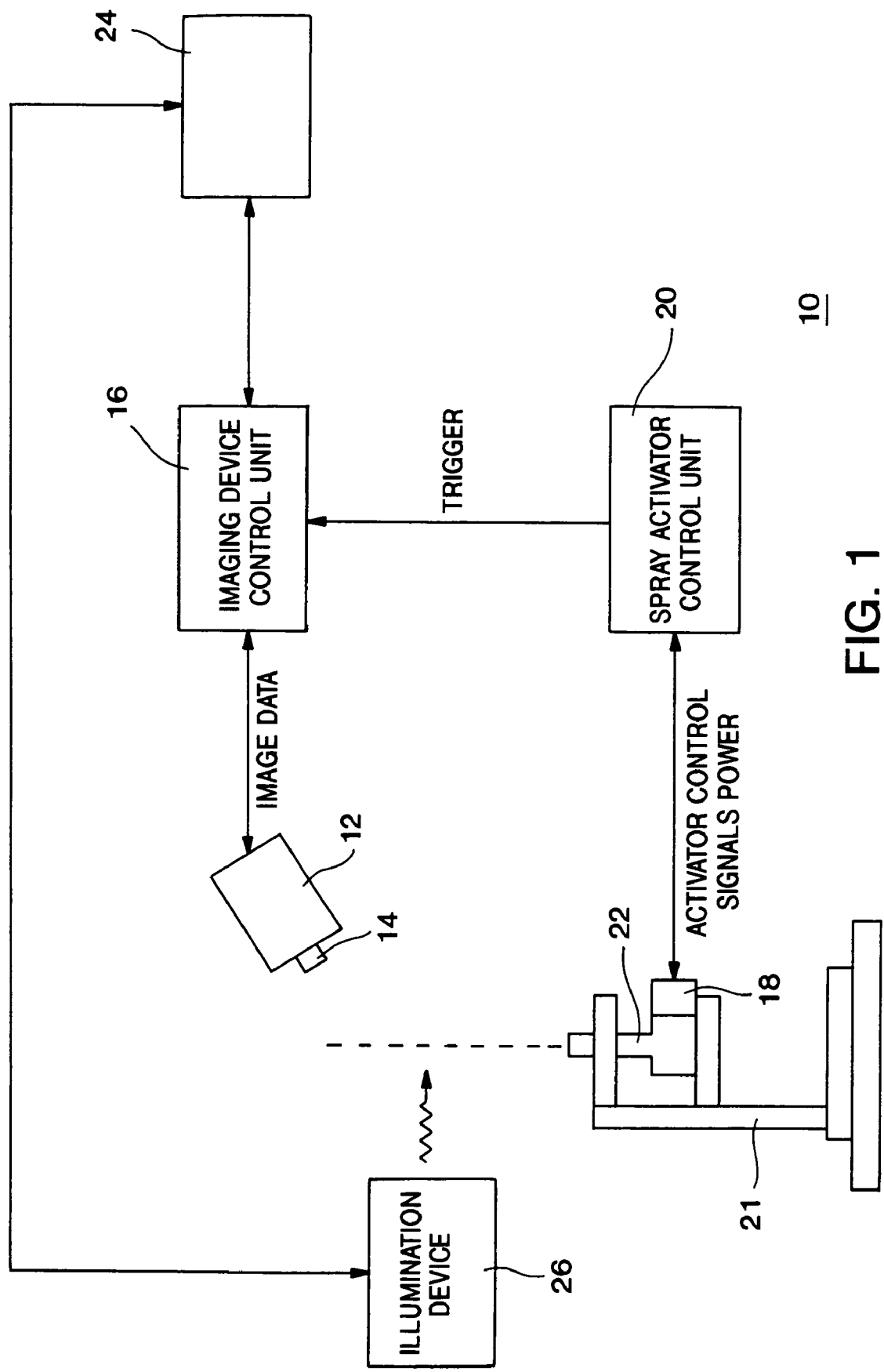
FIG. 1 is a schematic showing a spray data acquisition system, according to an embodiment of the invention.

FIG. 1 shows a spray data acquisition system 10 which generates data representative of the characteristics of an aerosol spray as emitted from a spray pump 22. The system 10 includes a spray pump housing 21 for the spray pump 22, an actuator 18, an illumination device 26 and an imaging device 12. The spray pump housing 21 is provided to position the spray pump 22 so as to direct an aerosol spray through a port in the housing 21 along a spray axis SA.

The imaging device 12 of the present invention's data acquisition system 10 includes a camera head 14 and a control unit 16. Associated with the actuator 18 is a spray actuator control unit 20 and a force control element 19, responsive to the spray control unit 20, for controlling a pumping force and a duration of an aerosol spray plume of the spray pump 22. The actuator 18 is preferably an electro-mechanical transducer that converts electrical control signals from the control unit 20, although other techniques known in the art for generating a pumping force may also be used, e.g., hydraulic, pneumatic, simple mechanical linkage, etc. The actuator 18 selectively activates the pump 22 to produce a spray plume for evaluation by the system 10. The centerline of the aerosol spray plume is shown as the spray axis SA.

The illumination device 26 is adapted to simultaneously or sequentially illuminate the spray with thin, fan-shaped beams of light along the spray axis SA and transverse to the spray axis SA. The imaging device 12 is adapted to acquire data representative of the optical density distribution of the portions of the spray illuminated by the illumination device 26. A first set of data is generated that is representative of a transverse cross-sectional slice of the spray plume. This set of data is useful in providing information relating to the spray divergence and the degree of spray uniformity in various directions radiating from the spray axis. A second set of data is generated that is representative of a slice of the spray along the spray axis. This set of data is useful in providing information on the spray divergence and the degree of spray uniformity along the spray axis and other axes diverging from the exit port.

The spray pump actuator 18, the force control element 19 and the control unit 20 are programmable so as to control key parameters associated with aerosol spray pumping, including pumping force and duration. In addition, the actuator 18 includes an output trigger signal that triggers the imaging device when the spray pump is actuated. Since the duration of the spray plume created by a single pumping of the pump 22 is only on the order of one second, it is crucial to have accurate synchronization between the spray pump actuator 18 and the imaging device 12. The InnovaSystems (Pennsauken, N.J.) Nasal Spray Pump Actuator is an example of a preferable actuator for use with the present invention. The InnovaSystems actuator includes built-in programmability to control many of the key parameters involved with aerosol spray pumping described herein. In addition, the InnovaSystems actuator is equipped with a digital output signal that can trigger the imaging device when the pump is fired. This signal is compatible with the digital input trigger of the National Instruments PCI-1424 and Dalsa CA-D6-0256 (an example of a preferable image acquisition device 12) and provides nearly perfect synchronization for the system 10.

The imaging device 12 is preferably capable of an image acquisition speed (i.e. framing rate) and spatial resolution to accurately capture the time evolution of a spray for both geometry and pattern testing. The imaging device 12 preferably provides a framing rate in the neighborhood of 1000 frames/second (fps) at a resolution of 256×256 pixels and 8-bit intensity to accurately capture the time evolution of the spray for both the plume geometry and spray pattern testing. Such acquisition speed and spatial resolution values result in an 80 to 100 fold increase in the amount of pertinent information about the complete fluid dynamics of an aerosol spray plume compared to the TLC-plate method currently being used. As described herein, the combination of the PCI-1424 image acquisition board from National Instruments (Austin, Tex.) and the CA-D6-0256 high speed digital camera from Dalsa (Waterloo, Ontario, Canada) is an example of a preferable imaging device 12. The CA-D6-0256 has a programmable framing rate from 1 to 955 fps at a resolution of 256 256 pixels with 256 grayscales (8-bit). In addition, the PCI-1424 image acquisition board communicates directly with the camera and is capable of acquiring and displaying these images in a computer-based software system. Additionally, the camera is fitted with a Cinegon lens from Schneider Optics (Hauppauge, N.Y.) that effectively focuses and transmits the laser light being reflected by the particles onto the camera's image sensor. The power and wavelength specification of the preferred illumination device (the Magnum 4000, described herein) matches favorably to the spectral response of the Cinegon lens and the Dalsa CA-D6-0256. Thus, the preferred camera and laser combination produces bright images that clearly show the spray particles.

The illumination device 26 is preferably capable of illuminating time-evolving spray particles at a frame rate of approximately 500 fps. Preferably, the illumination device is a continuous-wave illuminant (but can also be strobed in unison with the image acquisition to provide better freezing of the in-flight particles) such as a laser sheet generator. Furthermore, the light from the illumination device 26 is capable of being shaped into a thin sheet for accurate illumination of the particles for both the spray pattern and divergence angle measurements. Preferably, the illumination device is capable of producing approximately 4 W of illumination power and directly projecting a very thin sheet of light at a wavelength of 810 nm with a fan angle of 45° though other fan angles can be used depending on the situation. The Magnum 4000 laser sheet generator from Lasiris (St. Laurent, Quebec, Canada) is an example of a preferred illumination device 26. This solid-state diode laser produces 4 W of illumination power and directly projects a very thin sheet of light at a wavelength of 810 nm, and is available with fan angles of 30, 45 and 60°.

In one preferred embodiment, the mechanical mounting hardware for the spray data acquisition system 10 is designed so that spray pump housing, the spray pump actuator 18, the illumination device 26 and the imaging device 12 can be precisely, adjustably positioned and locked in place on a standard 2" thick optics bench. In this embodiment, the hardware also includes a custom designed calibration target to facilitate spatial calibration and perspective correction of the acquired images. In other embodiments, the various components of the spray data acquisition system 10 may be mounted relative to one another via other methods known to those in the art.

The control unit 16 of the imaging device 12 is responsive to the spray actuator control unit 20. In one embodiment, the control unit 16 of the imaging device 12 is connected to a computer system 24 for subsequent computer analysis of information acquired by the imaging device 12, so as to characterize the parameters associated with the spray plume being analyzed. Alternatively, the information gathered from the imaging device 12 can be analyzed according to other methods known to those of ordinary skill in the art.

In operation, the spray pump 22 is filled with test fluid and placed into the mouth of the actuator 18, which has been pre-calibrated for compression force and duration as per standard pharmaceutical spray testing guidelines. The imaging device 12 is set to capture at 500 fps giving a resolution of 256×256 pixels. The input trigger is armed and set to wait for the actuator 18 to fire. The illumination device 26 is turned on and its light sheet is focused to a thickness of approximately 1 mm when it illuminates the plane of spray particles.

Figure 2:
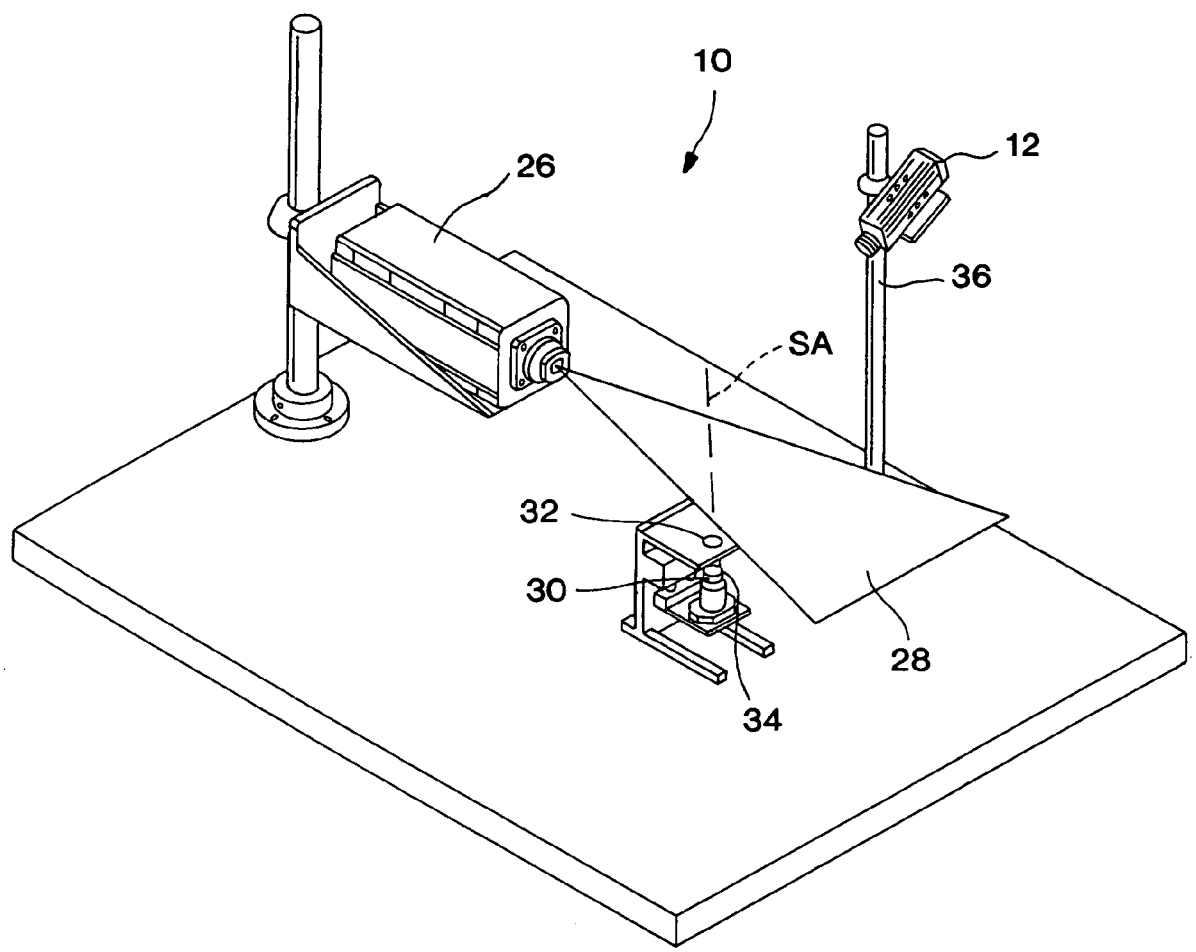
FIG. 2. shows an illumination device illuminating a transverse axial cross-sectional slice of a spray in the embodiment of FIG. 1.

When the spray data acquisition system 10 is used to conduct spray pattern tests, the illumination device 26 is positioned so that it illuminates in a thin sheet 28 a predetermined, transverse axial cross section of the spray directly downstream of the spray pump tip 30 as shown in FIG. 2. The centerline of the aerosol spray plume is shown as spray axis SA. The imaging device 12 is positioned so that it can view the spray pattern from above at a slight off-axis angle to prevent the spray particles from directly impinging on the imaging device 12 and lens 36. A calibration target 32 is then temporarily placed in the plane of the illumination device's light sheet 28 and the imaging device lens 36 is adjusted until the target 32 comes into focus. An image of the focused target 32 is then captured with the imaging device 12 and can be downloaded to a computer or analyzed mechanically according to methods known to those of ordinary skill in the art. This target image 32 is used as a basis for calibrating the physical coordinate system of the spray pattern images and to perform the necessary perspective correction to the images to account for the off-axis viewing angle. The target image 32 is then removed from the scene and the trigger 34 is fired on the actuator 18 causing the imaging device 12 to start capturing the time-evolving images of the spray pattern. This takes about 2 seconds. Alternatively, the images can be analyzed according to methods known to those of ordinary skill in the art.

Figure 3:
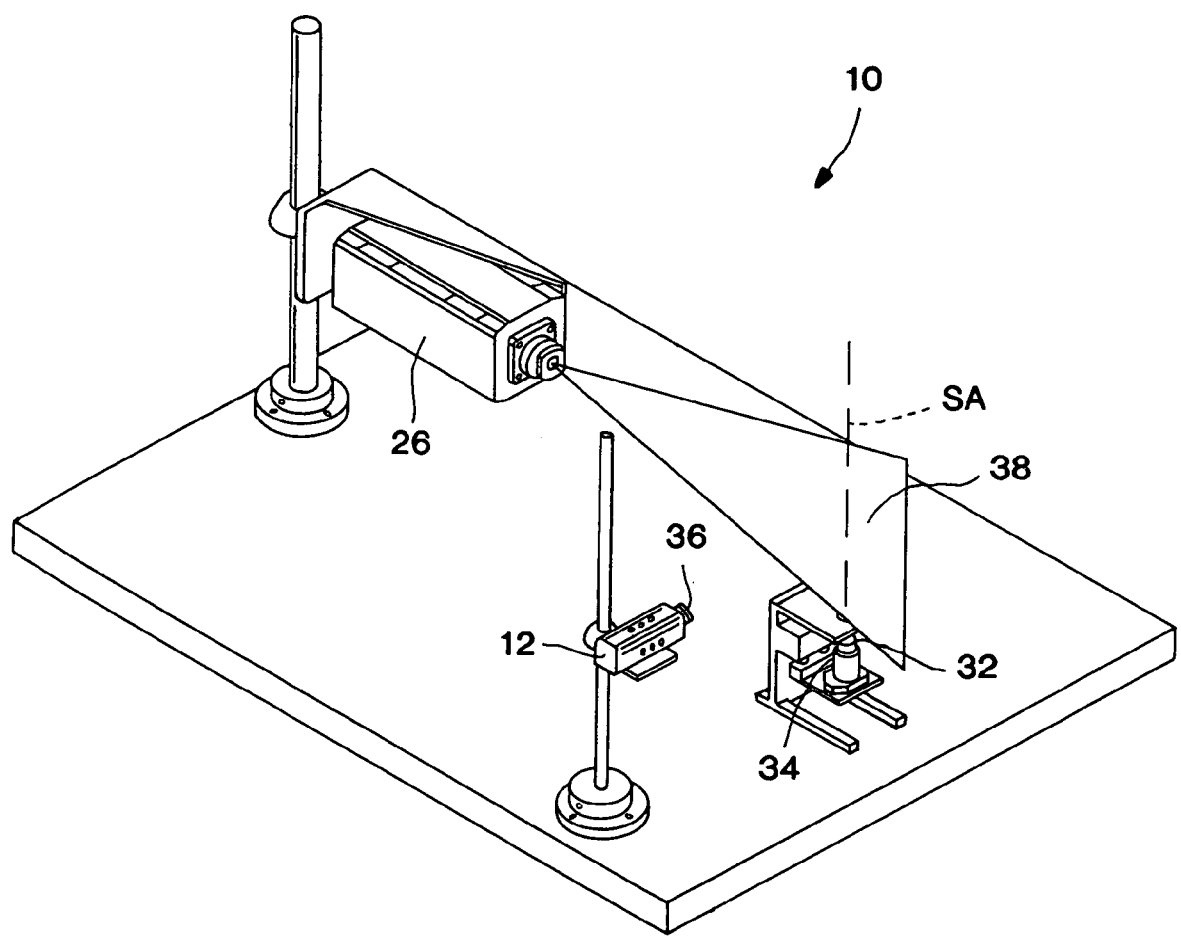
FIG. 3 shows an illumination device illuminating a slice of a spray along the spray axis in the embodiment of FIG. 1.

When the spray data acquisition system of the invention is used to conduct spray geometry tests, the illumination device 12 is positioned so that it illuminates a plane of particles parallel to the flow direction along the centerline of the spray or spray axis SA as shown in FIG. 3. The imaging device 12 is positioned perpendicular to the illumination device sheet plane 38. Similar to the spray pattern tests, the calibration target 32 is then temporarily placed in the plane of the sheet 38 of light emitted from the illumination device 26 and the imaging device lens 36 is adjusted until the target 32 comes into focus. Since in this case the imaging device 12 views the scene normally, no perspective correction is necessary so the target image 32 is used solely for calibrating the physical coordinate system of the spray geometry images. Again, the target image 32 is then removed from the scene and the actuator trigger 34 is fired. Alternatively, the images can be analyzed according to methods known to those of ordinary skill in the art.

The Spray VIEW Spray Characterization System User's Guide, Version 1.0, published by Image Therm Engineering, Inc., 1999, is an exemplary User's Manual for a spray data acquisition system according to the present invention. This user's guide is a manual for an entire spray characterization system, including information regarding acquisition, processing, set up, calibration, safety issues, et al. Thus, some of the information in the User's Manual is beyond the scope of this specification.

While this invention has been particularly shown and described with references to preferred embodiments thereof, it will be understood by those skilled in the art that various changes in form and details may be made therein without departing from the scope of the invention encompassed by the appended claims.

What is claimed is:

1. A spray data acquisition system comprising:
   an illumination device for illuminating a spray plume along at least one geometric plane that intersects the spray plume; and
   an imaging device for acquiring data representative of an interaction between the illumination and the spray plume along the at least one geometric plane;
   wherein the acquired data is representative of a first time-sequential set of images or a second time-sequential set of images, the first time-sequential set of images corresponding to an axial cross-sectional density characteristic along a first geometric plane substantially normal to a flow direction centerline and the second time-sequential set of images corresponding to a longitudinal density characteristic along a second geometric plane substantially parallel to and intersecting the flow direction centerline.

2. The spray data acquisition system according to claim 1, wherein the interaction between the illumination and the spray plume includes optical scattering.

3. The spray data acquisition system according to claim 1, wherein the interaction between the illumination and the spray plume includes optical absorption.

4. The spray data acquisition system according to claim 1, wherein the imaging device includes a digital imaging system for generating and recording the image data.

5. The spray data acquisition system according to claim 4, wherein the digital imaging system includes an image sampling rate of approximately 500 images per second.

6. The spray data acquisition system according to claim 1, wherein the illumination device includes a laser system having a fan-shaped output pattern.

7. The spray data acquisition system according to claim 6, wherein the fan-shaped output pattern includes a fan angle of approximately 45 degrees, and a laser line thickness of approximately one millimeter at approximately the centerline of the emitted spray.

8. A spray data acquisition system according to claim 1 wherein the illumination device illuminates the spray plume along a second geometric plane that intersects the spray plume, and the imaging device acquires data representative of a second interaction between the illumination and the spray plume along a second geometric plane.

9. A spray data acquisition system according to claim 8 wherein the first and the second geometric planes are substantially orthogonal.

10. A spray data acquisition system according to claim 1 further comprising a housing for supporting the pumping device.

* * * * *